United States Patent [19]

Adorante et al.

[11] Patent Number: 5,559,151

[45] Date of Patent: Sep. 24, 1996

[54] METHOD FOR REDUCING INTRAOCULAR PRESSURE IN THE MAMMALIAN EYE BY ADMINISTRATION OF CHLORIDE CHANNEL BLOCKERS

[75] Inventors: Joseph S. Adorante, Irvine; Elizabeth WoldeMussie, Laguna Niguel; Guadalupe Ruiz, Corona, all of Calif.

[73] Assignee: Allergan, Waco, Tex.

[21] Appl. No.: 346,660

[22] Filed: Nov. 30, 1994

[51] Int. Cl.$^6$ .................................................. A61K 31/195
[52] U.S. Cl. .......................... 514/567; 514/569; 514/737; 514/516; 514/912; 514/913; 424/78.04
[58] Field of Search .................................. 514/912, 913, 514/567, 569, 737, 516, 912, 913; 424/78.04

[56] References Cited

U.S. PATENT DOCUMENTS

| | | | |
|---|---|---|---|
| 4,981,871 | 1/1991 | Abelson | 514/913 |
| 4,994,493 | 2/1991 | Greger et al. | 514/567 |
| 5,435,998 | 7/1995 | Abelson | 514/913 |

OTHER PUBLICATIONS

T. L. Lewis and C. L. Chronister. Etiology and pathophysiology of primary open–angle glaucoma. In: Primary Care of the Glaucomas. T. L. Lewis and M. Fingeret, Editors. Appleton and Lance Publishers. 1993:65–80.

W. M. Hart. Intraocular Pressure. In: Adler's Physiology of the Eye. W. M. Hart, Editor. Mosby Year Book, Publisher. 1992: 248–267.

R. F. Brubaker. The physiology of aqueous humor formation. In: Glaucoma: Applied Pharmacology in Medical Treatment. S. M. Drance and A. H. Neufeld, Editors, Harcourt Brace Jovanovich, Publishers. 1984:35–70.

Biochimica et al Biophysica Acta, vol. 947, 1988, pp. 521–547, Gogelein, H., "Chloride channels in epithelia".

American Physiological Society, 1994, vol. 0363–6143, pp. C1210–C–1221, Edelman et al., "Ion transport asymmetry and functional coupling in bovine pigmented and nonpigmented ciliary epithelial cells".

Acta Physiol Scand: No. 149, 1993: pp. 365–376, Fryklund et al., "The effects of chloride transport inhibitors on intestinal fluid and ion transport in vivo and in vitro".

*Primary Examiner*—James H. Reamer
*Attorney, Agent, or Firm*—Robert J. Baran; Martin A. Voet; Howard R. Lambert

[57] ABSTRACT

Pharmaceutical compositions and a method are disclosed for treating glaucoma and/or ocular hypertension in the mammalian eye by administering to the mammalian eye the pharmaceutical composition of the invention which contains, as the active ingredient, one or more compounds having chloride channel blocking activity. Examples of chloride channel blockers utilized in the pharmaceutical composition and method of treatment are:

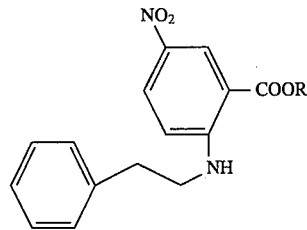

wherein R is hydrogen or a pharmaceutically-acceptable cation, e.g. an alkali or alkaline earth metal, or a quaternary amine; or R represents a ester-forming moiety, e.g. a lower alkyl radical, having up to six carbon atoms, that may be derived from a lower alkanol.

10 Claims, 2 Drawing Sheets

METHOD FOR REDUCING INTRAOCULAR PRESSURE IN THE MAMMALIAN EYE BY ADMINISTRATION OF CHLORIDE CHANNEL BLOCKERS

BACKGROUND OF INVENTION

1. Field of the Invention

The present invention is directed to pharmaceutical compositions, and primarily to topically applied ophthalmic compositions comprising as the active ingredient one or more compounds having the ability to block chloride channels in the ciliary epithelium, e.g. to inhibit the transport of chloride ions and fluid secretion in epithelia. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Art

Glaucoma is an optical neuropathy associated with elevated intraocular pressures which are too high for normal function of the eye, and results in irreversible loss of visual function. It is estimated in medical science that glaucoma afflicts approximately 2 percent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

The drugs currently utilized in the treatment of glaucoma include miotics (e.g., pilocarpine, carbachol, and acetylcholinesterase inhibitors), sympathomimetrics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of miotic drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue.

As a result additional antiglaucoma drugs are being developed, e.g., prostaglandin derivatives, muscarinic antagonists, etc.

In light of the foregoing circumstances, it is clear that a need exists for new, more potent antiglaucoma compositions which avoid or reduce the above-cited side effects and enhance patient compliance, since the foregoing and other anti-glaucoma and ocular hypotensive compounds and agents of the prior art do not provide a treatment or cure for glaucoma and ocular hypertension which is satisfactory in all respects. Therefore, the pharmacological and related arts and sciences continue searching for additional and better anti-glaucoma and ocular hypotensive agents.

Chloride channel blockers such as 5-nitro-2-(3-phenyl-propylamino)-benzoate (NPPB) have been shown to inhibit $Cl^-$ transport and fluid secretion/absorption in rat intestine. (See for example, Acta Physiol Scand: No. 149, 1993: pp. 365–376, Fryklund et al., "The effects of chloride transport inhibitors on intestinal fluid and ion transport in vivo and in vitro".)

SUMMARY OF THE INVENTION

Surprisingly it has been discovered in accordance with the present invention that chloride channel blockers are effective as anti-glaucoma agents and as agents for reducing intraocular pressure, when such agents are applied to the mammalian eye in a pharmaceutical composition, preferably in a topical ophthalmic composition. Accordingly, the present invention relates to a method of treating glaucoma, or ocular hypertension by topically administering to the mammalian eye an ophthalmic composition which contains an effective amount of a chloride channel blocker. A preferred example of chloride channel blockers suitable as the active ingredients of the ophthalmic compositions of the invention are:

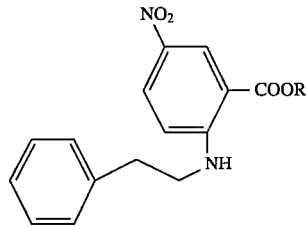

wherein R is hydrogen or a pharmaceutically-acceptable cation, e.g. an alkali ion, or a quarternary amine; or R represents a ester-forming moiety, e.g. a lower alkyl radical, having up to six carbon atoms, i.e. a radical that may be derived from a lower alkanol.

While not wishing to be bound by theory it is believed that in ciliary epithelium, i.e. the tissue mediating aqueous humor secretion, movement of fluid into the aqueous chamber, is in part orchestrated by $K^+$ and $Cl^-$ channels residing in the nonpigmented (NPE) cells. (See for example, American Journal of Physiology, 1994, Vol. 0363–6143, pp C1210–C-1221, Edelman et al, "Ion transport asymmetry and functional coupling in bovine pigmented and nonpigmented ciliary epithelial cells".) Thus, aqueous secretion is inhibited and hence intraocular pressure (IOP) is lowered by blocking $Cl^-$ channels in the NPE cells.

The ophthalmic compositions of the invention contain the active ingredient in a concentration range of approximately 0.0001 to 0.1 percent weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

DETAILED DESCRIPTION OF THE INVENTION

Figure 1:
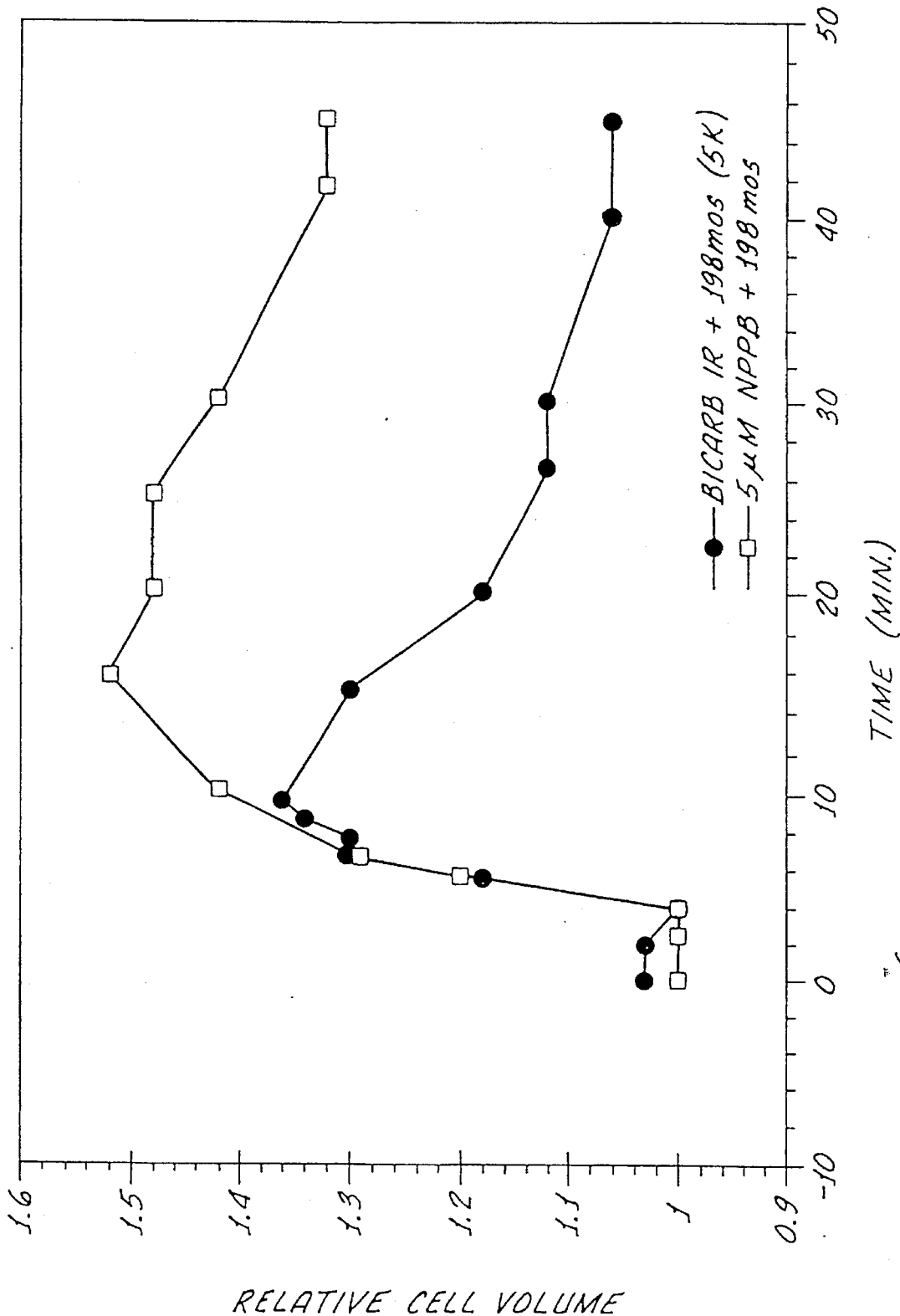
FIG. 1 is a graph showing the effect of the presence of the drug NPPB on the regulatory volume decrease (RVD) of a suspension of cultured human non-pigmented ciliary epithelial (NPE) cells.

The compounds which are utilized in accordance with the method of the present invention, and in the pharmaceutical compositions of the present invention, are chloride channel blockers. In this regard the term chloride channel blocker is defined as those compounds or agents which inhibit net Cl flux (current) through a Cl specific pathway (channel, integral membrane protein) within biological membranes. Specific and preferred examples of chloride channel blockers which are utilized in accordance with the present invention are provided below.

Pharmaceutically acceptable salts of the chloride channel blockers can also be used in accordance with the present invention. A pharmaceutically acceptable salts may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, such as alkali ions, e.g. sodium, potassium, etc. Organic amine salts may be made with amines, particularly ammonium salts such as mono-, di- and trialkyl amines, e.g. alkyl amines wherein each alkyl group may comprise up to six carbon atoms, or ethanol amines. Salts may also be formed with caffeine, tromethamine and similar molecules. It is only important that the cation of any salt of a chloride channel blocker utilized in the compositions or methods of this invention be able to block chloride channels in the ciliary epithelium.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water), saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 1% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly in to the eye. Particularly useful results are obtained when the compound or compounds are applied topically to the eye in an ophthalmic solution, i.e. as ocular drops.

Topical ophthalmic preparations, for example ocular drops, gels or creams, are preferred because of ease of application, ease of dose delivery and fewer systemic side effects, such as cardiovascular hypotention. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose and hydroxyethyl cellulose.

Tonicity adjustors may be added as needed or convenient. They include, but are not limited to, salts, particularly sodium chloride, potassium chloride etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the chloride channel blocker as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Specific examples of chloride channel blockers which are used as the active effective ingredients in the ophthalmic compositions of the present invention are described and shown below: N-phenylanthranilic acid, DPC (diphenylamine-2-carboxylic acid), IAA-94 (R(+)-methylindazone, indanyloxyacetic acid 94), 2-aminomethyl phenols such as MK-447 (2-aminomethyl-4-(1,1-dimethyl ethyl)-6-iodophenol hydrochloride (2) disulfonic stilbenes such as DIDS (4,4'-diisothiocyanostilbene-2,2'-disulfonic acid).

Alternatively, a chloride channel blocker may be defined as a pharmaceutical compound showing activity in the following assay:

Inhibition of current mediated by Cl ions using patch clamp technology in the whole cell, cell attached or cell excised mode. (See for Example, Biochimica et al Biophysica Acta, Vol. 947, 1988, pp. 521–547, Gogelein, H., "Chloride channels in epithelia".)

EXAMPLES

The present invention is demonstrated by in vitro and in vivo data. In FIG. 1, 5 μM NPPB were found to depress the regulatory volume decrease (RVD) that occurs following hyposmotic swelling of cultured human non-pigmented ciliary epithelial (NPE) cells. In this example, NPE cells were suspended in an isosmotic (290 mOsm) solution containing 5 μM NPPB for 30 minutes prior to suspension in a hyposmotoic (198 mOsm) solution. Control cells were subjected to the same hyposmotic solution but without NPBB in the medium. Changes in cell volume were measured using a Coulter Counter interfaced to a Coulter Channelyzer. It is noted that, following osmotic swelling, control cells regulate towards their original isosmotic volume while NPBB-treated cells remain swollen. The above findings indicate that intracellular NPBB, via blocking of the chloride channel, inhibits solute and osmotically obliged H$_2$O efflux. Because the chloride-dependent ion flux pathways, activated following osmotic cell swelling of NPE cells, are involved in aqueous secretion, NPBB will inhibit aqueous humor formation and, thus, lower IOP.

Figure 2:
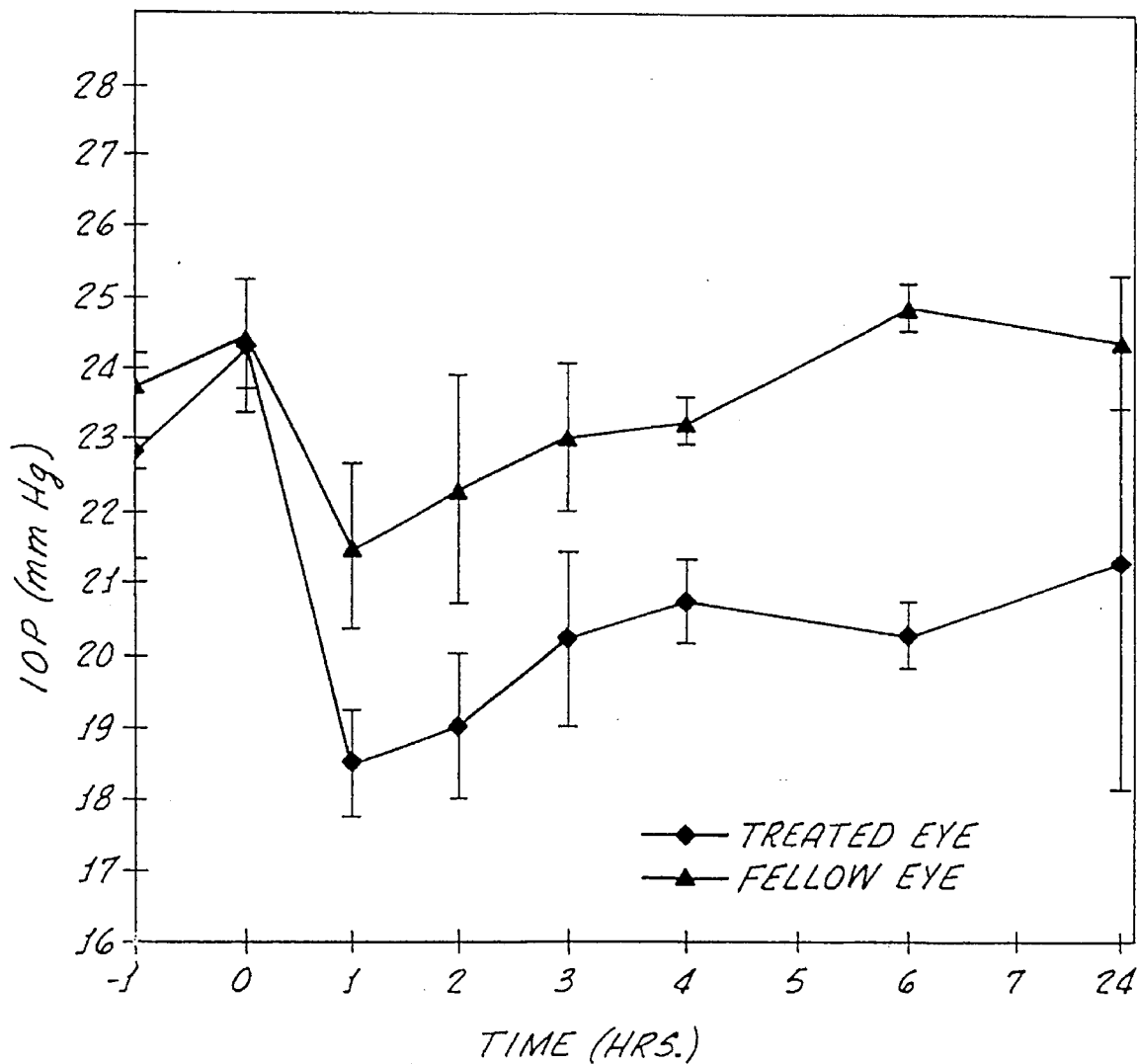
FIG. 2 is a graph showing the effect of intracameral administration of the drug NPPB on the intraocular pressure (IOP) in the rabbit eye.

In the in vivo studies normotensive rabbits were injected intracamerally with 100 μM NPBB. FIG. 2 shows that 100 μM NPBB lowered IOP by 7 mm of Hg and IOP remained depressed for 24 hours. Taken together, the above in vitro and in vivo experiments demonstrate that blocking the chloride ion channel in the ciliary epithelium will reduce IOP.

One advantage Cl⁻ channel inhibition has over other IOP lowering therapies is that the effector, i.e. the ion channel, is targeted rather than the receptor. Since effector blockage is direct, it should be the most potent and effective way of inhibiting aqueous secretion and hence lowering IOP. On the other hand, targeting a receptor to block an effector is indirect and relies on modulation of a series of cellular events (intracellular messengers/signals) prior to effector inhibition.

In view of the above, it is clear that the scope of the present invention should be interpreted solely on the basis of the following claims, as such claims are read in light of the disclosure.

What is claimed is:

1. A method of treating animals of the mammalian species, including humans, for the purpose of reducing introacular pressure in the eye of the mammal comprising the step of administering to the mammal a pharmaceutical composition which comprises as its active ingredient a compound having chloride channel blocking activity, wherein said compound is selected from the group consisting of compounds represented by the formula:

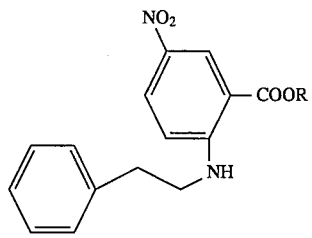

wherein R is hydrogen or a pharmaceutically-acceptable cation of R represents a easter-forming moiety.

2. The method of treatment of claim 1 where the composition is an ophthalmic solution adapted for administration to the eye of a mammal in the form of eye droplets.

3. The method of treatment of claim 2 wherein in the ophthalmic composition the concentration of the compound having chloride channel blocking activity is in the range of approximately 0.0001 to 1 percent weight by volume.

4. A method of treating animals of the mammalian species, including humans, for the purpose of reducing intraocular pressure in the eye of the mammal comprising the step of administering to the mammal an ophthalmic composition which comprises as its active ingredient one or more compounds having chloride channel blocking activity compounds selected from the group consisting of N-phenylanthranilic acid, DPC (diphenylamine-2-carboxylic acid), IAA-94 (R(+)-methylindazone, indanyloxyacetic acid 94), 2-aminomethyl phenols such as MK-447 (2-aminomethyl-4-(1,1-dimethyl ethyl)-6-iodophenol hydrochloride (2) disulfonic stilbenes such as DIDS (4,4'-diisothiocyanostilbene-2-2'-disulfonic acid) and 5-nitro-2(3 phenyl propyl amino)-benzoate (NPPB).

5. The method of treatment of claim 4 wherein the composition is an ophthalmic solution adapted for administration to the eye of a mammal in the form of eye droplets.

6. The method of claim 1 wherein R is hydrogen, or an alkali metal ion, or a quaternary amine selected from the group consisting of mono-, di- and trialkyl amines, wherein each alkyl group may comprise up to six carbon atoms, or ethanol amine, or caffeine, or tromethamine, or a lower alkyl radical having up to six carbon atoms.

7. The method of treatment of claim 5 wherein in the ophthalmic composition the concentration of the compound having chloride channel blocking activity is in the range of approximately 0.0001 to 1 percent weight by volume.

8. A method for providing neuroprotective effect to the eye of a mammal which comprises the step of administering to the mammal a pharmaceutical composition which comprises as its active ingredient one or more compounds having chloride channel blocking activity wherein said compound having a chloride channel blocking activity is selected from the group consisting of N-phenylanathracilic acid, DPC (diphenylamine-2-carboxylic acid), IAA-94 (R+)-methylidazone, indanyloxyacetic, acid 94), MK-447 (2-aminoemethyl-4-(1,1 -dimethyl ethyl)-6-iodophenol hydrochloride, DIDS (4,4'-diisothiocyanostilbene- 2,2'-disulfonic acid) and compounds represented by the formula:

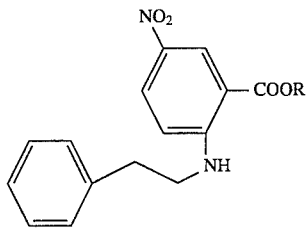

wherein R is hydrogen or a pharmaceutically-acceptable cation, or R represents a ester-forming moiety.

9. The method of claim 8 wherein the composition contains approximately 0.0001 to 1 percent weight by volume of said compound having chloride channel blocking activity.

10. The method of claim 8 wherein R is hydrogen, or an alkali metal ion, or a quaternary amine selected from the group consisting of mono-, di- and trialkyl amines, wherein each alkyl group may comprises up to six carbon atoms, or ethanol amine, or caffeine, or tromethamine, or a lower alkyl radical having up to six carbon atoms.

* * * * *

UNITED STATES PATENT AND TRADEMARK OFFICE
CERTIFICATE OF CORRECTION

PATENT NO. : 5,559,151
DATED : 9/24/1996
INVENTOR(S) : Adorante et al

It is certified that error appears in the above-indentified patent and that said Letters Patent is hereby corrected as shown below:

Column 2, line 46; delete "nonpigmented" and insert in place thereof --non-pigmented ciliary epithelial--

Column 4, line 14; delete "in to" and insert in place thereof --into--

Column 5, lines 29 and 30; put in italics "in vivo" and "in vitro"

Column 5, lines 50, 53 and 54; put in italics "in vivo" and "in vitro"

Column 3, line 21; delete "salts" and insert in place thereof --salt--

Column 5, line 24; delete "Example" and insert in place thereof --example--

Column 6, line 22; delete "of" and insert in place thereof --or--

Column 6, line 22; delete "easter" and insert in place thereof --ester--

Column 6, line 41; delete "(2)" and insert in place thereof --or--

Column 6, line 64; delete "phenylanathracilic" and insert in place thereof --phenylanthranilic--

Column 6, line 66; delete "methylidazone" and insert in place thereof --methylindazone--

UNITED STATES PATENT AND TRADEMARK OFFICE
CERTIFICATE OF CORRECTION

PATENT NO. : 5,559,151
DATED : 9/24/1996
INVENTOR(S) : Adorante et al

It is certified that error appears in the above-indentified patent and that said Letters Patent is hereby corrected as shown below:

Column 6, line 67; delete "aminoemethyl" and insert in place thereof
--aminomethyl--
Column 8, line 10; delete "comprises" and insert in place thereof --comprise--

Signed and Sealed this

Eighteenth Day of March, 1997

*Attest:*

BRUCE LEHMAN

*Attesting Officer*     *Commissioner of Patents and Trademarks*